United States Patent [19]

Thomas et al.

[11] Patent Number: 4,599,448
[45] Date of Patent: Jul. 8, 1986

[54] NOVEL N-(1-ALKENYL)-CHLOROACETANILIDES AS HERBICIDES AND PLANT GROWTH REGULATORS

[75] Inventors: Rudolf Thomas, Wuppertal; Ludwig Eue, Leverkusen; Robert Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 579,834

[22] Filed: Feb. 13, 1984

Related U.S. Application Data

[63] Continuation of Ser. No. 375,062, May 5, 1982, abandoned.

[30] Foreign Application Priority Data

May 26, 1981 [DE] Fed. Rep. of Germany ....... 3120990

[51] Int. Cl.$^4$ ............................................. C07C 103/34
[52] U.S. Cl. ........................................ 564/214; 71/118
[58] Field of Search ........................... 71/118; 564/214

[56] References Cited

U.S. PATENT DOCUMENTS

Re. 26,961 10/1970 Hamm et al. .......................... 71/118
4,277,278 7/1981 Eicken et al. .......................... 71/118

FOREIGN PATENT DOCUMENTS 1116607 1/1982 Canada ................................... 71/118
0008057 2/1980 European Pat. Off. .............. 71/118
0018509 4/1980 European Pat. Off. .
0010972 5/1980 European Pat. Off. .
0037019 10/1981 European Pat. Off. .............. 71/118
2042497 3/1972 Fed. Rep. of Germany .
2835157 8/1978 Fed. Rep. of Germany .

*Primary Examiner*—Paul J. Killos
*Attorney, Agent, or Firm*—Sprung Horn Kramer & Woods

[57] ABSTRACT

N-(Alkenyl)-chloroacetanilides of the formula

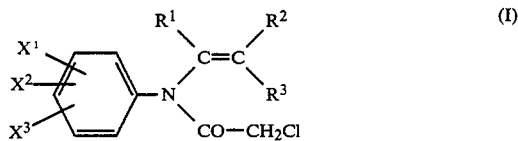

in which
  $R^1$ represents a hydrogen atom or an alkyl group,
  $R^2$ represents a hydrogen atom or an alkyl, alkoxy, alkoxyalkyl, hydroxyalkyl or benzyl group,
  $R^3$ represents a hydrogen atom or an alkyl, alkenyl, alkoxy, alkoxyalkyl, alkylcarbonyl, alkylcarbonylalkyl, alkoxycarbonyl or alkoxycarbonylalkyl group, or
  $R^1$ and $R^2$, together with the C=C double bond, represent an optionally substituted mono-unsaturated or polyunsaturated ring which can also contain heteroatoms, or
  $R^2$ and $R^3$, together with the adjacent carbon atom, represent an optionally substituted, saturated or unsaturated ring which can also contain heteroatoms and/or a carbonyl group, or
  $R^2$ and $R^3$ together represent a radical of the formula

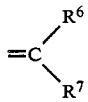

wherein
  $R^6$ represents a hydrogen atom or an alkyl group and
  $R^7$ represents an alkyl or phenyl group and
  $X^1$, $X^2$ and $X^3$ independently of one another represent a hydrogen or halogen atom or an alkyl group, which possess herbicidal and plant growth regulating properties.

12 Claims, No Drawings

NOVEL N-(1-ALKENYL)-CHLOROACETANILIDES AS HERBICIDES AND PLANT GROWTH REGULATORS

This is a continuation of application Ser. No. 375,062, filed May 5, 1982, now abandoned.

The present invention relates to certain new N-(1-alkenyl)-chloroacetanilides, to a process for their use as herbicides and as plant growth regulators.

It has already been disclosed that many chloroacetanilides possess herbicidal properties. Thus, for example, 2,6-diethyl-N-methoxymethyl-chloroacetanilide can be used for combating weeds (see U.S. Pat. No. 3,442,945). However, the action of this compound is not always completely satisfactory and, in particular, its use as a selective herbicide is only possible to a limited extent in the case of many cultivated plants.

The present invention now provides, as new compounds, N-(1-alkenyl)-chloroacetanilides of the general formula

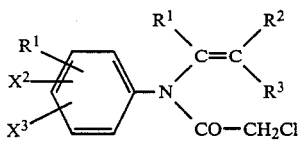

in which
R$^1$ represents a hydrogen atom or an alkyl group,
R$^2$ represents a hydrogen atom or an alkyl, alkoxy, alkoxyalkyl, hydroxyalkyl or benzyl group,
R$^3$ represents a hydrogen atom or an alkyl, alkenyl, alkoxy, alkoxyalkyl, alkylcarbonyl, alkylcarbonylalkyl, alkoxycarbonyl or alkoxycarbonylalkyl group or
R$^1$ and R$^2$, together with the C=C double bond, represent an optionally substituted monounsaturated or polyunsaturated ring which can also contain hetero-atoms and/or a carbonyl group, or
R$^2$ and R$^3$, together with the adjacent carbon atom, represent an optionally substituted, saturated or unsaturated ring which can also contain heteroatoms, or
R$^2$ and R$^3$ together represent a radical of the general formula

wherein
R$^6$ represents a hydrogen atom or an alkyl group and
R$^7$ represents an alkyl or phenyl group and
X$^1$, X$^2$ and X$^3$ independently of one another represent a hydrogen or halogen atom or an alkyl group.

According to the present invention we provide a process for the production of a compound of the present invention, characterized in that an azine of the general formula

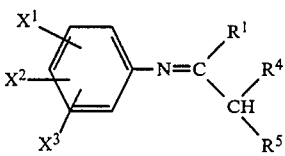

in which
R$^1$, X$^1$, X$^2$ and X$^3$ have the meanings given above,
R$^4$ represents a hydrogen atom or an alkyl, alkoxy, alkoxyalkyl, hydroxyalkyl or benzyl group and
R$^5$ represents a hydrogen atom or an alkyl, alkenyl, alkoxy, alkoxyalkyl, alkylcarbonyl, alkylcarbonylalkyl, alkoxycarbonyl or alkoxy-carbonylalkyl group, or
R$^1$ and R$^4$, together with the adjacent C—C bond, represent an optionally substituted, saturated or unsaturated ring which can also contain heteroatoms and/or a carbonyl group, or
R$^4$ and R$^5$, together with the adjacent carbon atom, represent an optionally substituted, saturated or unsaturated ring which can also contain heteroatoms, or
R$^4$ and R$^5$ together represent a radical of the general formula

wherein
R$^6$ and R$^7$ have the meanings given above,
is reacted with a chloroacetyl halide of the general formula $$\text{Hal—CO—CH}_2\text{—Cl} \qquad \text{(III)}$$

in which
Hal represents a chlorine or bromine atom,
if appropriate in the presence of a diluent, and the resulting chloroacetanilide of the general formula

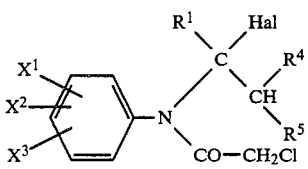

in which
R$^1$, R$^4$, R$^5$, X$^1$, X$^2$, X$^3$ and Hal have the meanings given above,
is subjected, without preliminary isolation, to an elimination of hydrogen halide, if appropriate in the presence of a base.

In addition, it has been found that the compounds of the present invention have good herbicidal properties, in particular selective herbicidal properties. In addition, they are very suitable for use in regulating plant growth.

Surprisingly, the compounds according to the present invention are more promising for use as selective agents for combating weeds, and have a comparably good general action against weeds, in comparison with the known 2,6-diethyl-N-methoxymethylchloroacetanilide which is a similar compound chemically and with respect to its action. Furthermore, the compounds according to the invention surprisingly also possess a powerful plant growth-regulating activity.

Preferred compounds according to the present invention are those in which

- $R^1$ represents a hydrogen atom or a straight-chain or branched alkyl group having 1 to 4 carbon atoms;
- $R^2$ represents a hydrogen atom, a straight-chain or branched alkyl group having 1 to 4 carbon atoms, an alkoxy group having 1 to 4 carbon atoms, a hydroxyalkyl group having 1 to 4 carbon atoms, an alkoxyalkyl group having 1 to 4 carbon atoms in the alkyl part and 1 to 4 carbon atoms in the alkoxy part, or a benzyl group;
- $R^3$ represents a hydrogen atom, a straight-chain or branched alkyl group having 1 to 4 carbon atoms, an alkoxy group having 1 to 4 carbon atoms, an alkoxyalkyl group having 1 to 4 carbon atoms in the alkyl part and 1 to 4 carbon atoms in the alkoxy part, an alkylcarbonyl group having 1 to 4 carbon atoms in the alkyl part, an alkylcarbonylalkyl group having 1 to 4 carbon atoms in each alkyl part, an alkoxycarbonyl group having 1 to 4 carbon atoms in the alkoxy part, an alkoxycarbonylalkyl group having 1 to 4 carbon atoms in the alkoxy part and 1 to 4 carbon atoms in the alkyl part or a straight-chain or branched alkenyl group having 2 to 6 carbon atoms; or
- $R^1$ and $R^2$, together with the C=C double bond, represent an optionally monosubstituted or polysubstituted, mono-unsaturated or poly-unsaturated, 5-membered or 6-membered ring which can contain one or two hetero-atoms (the following being mentioned as examples of substituents: alkyl having 1 to 4 carbon atoms, halogen and hydroxy) and/or a carbonyl group, or
- $R^2$ and $R^3$, together with the adjacent carbon atom, represent an optionally monosubstituted or polysubstituted, saturated or unsaturated, 5-membered or 6-membered ring which can contain one or two hetero-atoms (the following being mentioned as examples of substituents: alkyl having 1 to 4 carbon atoms, halogen and hydroxy), or
- $R^2$ and $R^3$ together represent a radical of the general formula

wherein
- $R^6$ represents a hydrogen atom or an alkyl group having 1 to 4 carbon atoms and
- $R^7$ represents an alkyl group having 1 to 4 carbon atoms or a phenyl group;
- $X^1$, $X^2$ and $X^3$ independently of one another, represent a hydrogen, fluorine, chlorine or bromine atom or a straight-chain or branched alkyl group having 1 to 4 carbon atoms.

Particularly preferred compounds of the present invention are those in which

- $R^1$ represents a hydrogen atom or a methyl, ethyl or isopropyl group;
- $R^2$ represents a hydrogen atom, or a methyl ethyl, isopropyl, methoxy, ethoxy, isopropoxy, methoxymethyl, ethoxymethyl, iso-hydroxypropyl or benzyl group;
- $R^3$ represents a hydrogen atom or a methyl, ethyl, isopropyl, methoxy, ethoxy, isopropoxy, methoxymethyl, ethoxymethyl, methylcarbonyl, ethylcarbonyl, methylcarbonylmethyl, methoxycarbonyl, ethoxycarbonyl or methoxycarbonylmethyl group or a straight-chain or branched alkenyl group having 2 to 4 carbon atoms; or
- $R^1$ and $R^2$, together with the C=C double bond, represent a mono-unsaturated or poly-unsaturated, 5-membered or 6-membered ring which is optionally substituted by methyl, ethyl, hydroxyl and/or chlorine and which can contain one or two hetero-atoms (such as oxygen, nitrogen and/or sulphur) and/or a carbonyl group, or
- $R^2$ and $R^3$, together with the adjacent carbon atom, represent a saturated or unsaturated, 5-membered or 6-membered ring which is optionally substituted by methyl, ethyl, hydroxy and/or chlorine and which can contain one or two hetero-atoms (such as oxygen, nitrogen and/or sulphur), or
- $R^2$ and $R^3$ together represent the radical of the general formula

wherein
- $R^6$ represents a hydrogen atom or a methyl or ethyl group and
- $R^7$ represents a methyl, ethyl or phenyl group;
- $X^1$, $X^2$ and $X^3$, independently of one another represent a hydrogen, chlorine or fluorine atom or a methyl, ethyl, isopropyl, isobutyl, sec.-butyl, tert.-butyl group.

If, for example, N-ethylidene-2,6-diethylaniline and chloroacetyl chloride are used as the starting materials, the course of the reaction, of the process according to the invention is illustrated by the following equation:

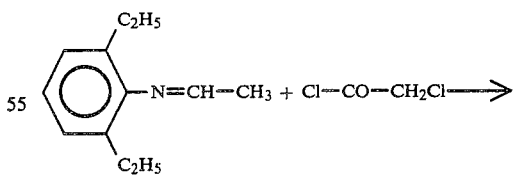

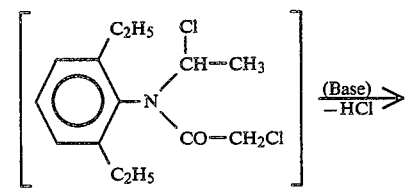

(not isolated)

-continued

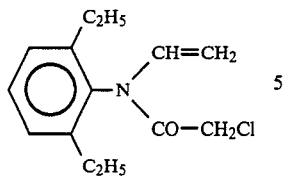

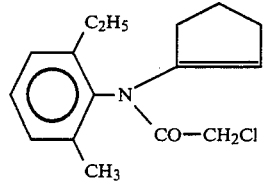

If, for example, N-(3-cyclohexenyl-methylidene)-2,6-dimethylaniline and chloroacetyl chloride are used as the starting materials, the course of the reaction of the process according to the invention is illustrated by the following equation:

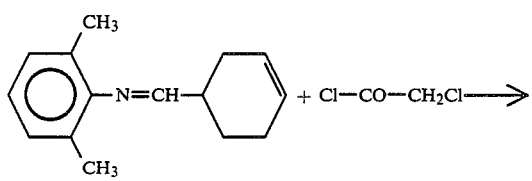

If, for example, N-(cyclopentylidene)-2-ethyl-6-methylaniline and chloroacetyl chloride are used as the starting materials, the course of the reaction of the process according to the invention is illustrated by the following equation:

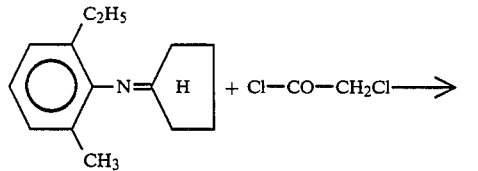

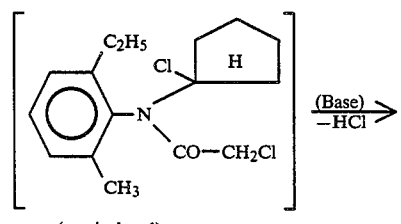

(not isolated)

Preferred azines of formula (II) to be used as the starting materials for the reaction according to the invention are those in which $R^1$, $X^1$, $X^2$ and $X^3$ represent those radicals which have already been mentioned in connection with the description of the preferred compounds according to the invention, $R^4$ represents a hydrogen atom, a straight-chain or branched alkyl group having 1 to 4 carbon atoms, an alkoxy group having 1 to 4 carbon atoms, a hydroxyalkyl group having 1 to 4 carbon atoms, an alkoxyalkyl group having 1 to 4 carbon atoms in the alkyl part and 1 to 4 carbon atoms in the alkoxy part, or benzyl, $R^5$ represents a hydrogen atom, a straight-chain or branched alkyl group having 1 to 4 carbon atoms, an alkoxy group having 1 to 4 carbon atoms, an alkoxyalkyl group having 1 to 4 carbon atoms in the alkyl part and 1 to 4 carbon atoms in the alkoxy part, an alkylcarbonyl group having 1 to 4 carbon atoms in the alkyl part, an alkylcarbonyl-alkyl group having 1 to 4 carbon atoms in each alkyl part, an alkoxycarbonyl group having 1 to 4 carbon atoms in the alkoxy part, an alkoxycarbonylalkyl having 1 to 4 carbon atoms in the alkoxy part and 1 to 4 carbon atoms in the alkyl part, or a straight-chain or branched alkenyl group having 2 to 6 carbon atoms, or $R^1$ and $R^4$, together with the adjacent C—C bond, additionally represent an optionally monosubstituted or polysubstituted, saturated or unsaturated, 5-membered or 6-membered ring which can contain one or two hetero-atoms and/or a carbonyl group (the following being mentioned as examples of substituents: alkyl having 1 to 4 carbon atoms, halogen and hydroxyl), or $R^4$ and $R^5$, together with the adjacent monosubstituted or polysubstituted, saturated or unsaturated, 5-membered or 6-membered ring which can contain one or two hetero-atoms (the following being mentioned as examples of substituents: alkyl having 1 to 4 carbon atoms, halogen and hydroxyl), or $R^4$ and $R^5$ together also represent a radical of the general formula

wherein $R^6$ represents a hydrogen atom or an alkyl group having 1 to 4 carbon atoms and $R^7$ represents an alkyl group having 1 to 4 carbon atoms or a phenyl group.

Particularly preferred starting materials of formula (II) are those compounds, in which $R^1$, $X^1$, $X^2$ and $X^3$ have those meanings which have already been mentioned in connection with the description of the particularly preferred compounds according to the invention, $R^4$ represents a hydrogen or a methyl, ethyl, isopropyl, methoxy, ethoxy, isopropoxy, methoxymethyl, ethoxymethyl, iso-hydroxypropyl or benzyl group;

$R^5$ represents a hydrogen atom or a methyl, ethyl, isopropyl, methoxy, ethoxy, isopropoxy, methoxymethyl, ethoxymethyl, methylcarbonyl, ethylcarbonyl, methylcarbonylmethyl, methoxycarbonyl, ethoxycarbonyl, or methoxycarbonylmethyl group or a straight-chain or branched alkenyl group having 2 to 4 carbon atoms; or $R^1$ and $R^4$, together with the adjacent C—C bond, represent a saturated or unsaturated 5-membered or 6-membered ring which is optionally substituted by methyl, ethyl, hydroxyl, and/or chlorine and which can contain one or two hetero-atoms (such as oxygen, nitrogen and/or sulphur) and/or a carbonyl group, or $R^4$ and $R^5$, together with the adjacent carbon atom, represent a saturated or unsaturated, 5-membered or 6-membered ring which is optionally substituted by methyl, ethyl, hydroxyl, and/or chlorine and which can contain one or two hetero-atoms (such as oxygen, nitrogen and/or sulphur), or $R^4$ and $R^5$ together represent a radical of the general formula

wherein $R^6$ represents a hydrogen atom or a methyl, or ethyl group, and $R^7$ represents a methyl, ethyl or phenyl group.

Azines of the formula (II) are known and can be prepared in a simple manner by processes which are known in principle (see DE-OS (German Published Specification) No. 1,670,859 and DE-OS (German Published Specification) No. 3,011,084). Thus, the azines of the formula (II) can be synthesized by reacting an aniline of the general formula

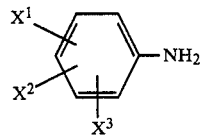 (V)

in which $X^1$, $X^2$ and $X^3$ have the meanings given above, with an aldehyde or ketone of the general formula

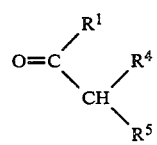 (VI)

in which $R^1$, $R^4$ and $R^5$ have the meanings given above, it being possible for the compounds of the formula (VI) optionally also to be present in the form of their acetals or ketals, if appropriate in the presence of an inert organic solvent (such as methylene chloride or toluene) and, if appropriate, in the presence of a basic or acid catalyst (such as dimethylbenzylamine or p-toluene-sulphonic acid) at a temperature between $-10°$ C. and $+120°$ C. (see also the preparative examples hereinbelow).

Formula (III) gives the definition of the chloroacetyl halides further required as starting materials in the process according to the invention. The particular chloroacetyl halides are known.

Suitable diluents for the process according to the invention are inert organic solvents. These preferably include ketones (such as acetone and methyl ethyl ketone), nitriles (such as acetonitrile), ethers (such as tetrahydrofuran or dioxane), esters (such as ethyl acetate) halogenated hydrocarbons (such as methylene chloride) and, especially aromatic hydrocarbons (such as benzene and toluene).

In carrying out the first stage of the process according to the invention, the reaction temperatures can be varied within a relatively wide range. In general, the reaction is carried out at a temperature between $-20°$ and $+150°$ C., preferably between $-20°$ and $+100°$ C.

The elimination of hydrogen halide in the second stage of the process according to the invention is effected in a generally customary and known manner. As a rule, the following procedure is followed: without preliminary isolation of the compounds of the formula (IV), the reaction mixture is heated or a base is added at the abovementioned temperatures.

Any of the acid acceptors which are customarily suitable for reactions of this type can be employed as bases in this process. The following are preferably used: alkali metal carbonates (such as sodium and potassium carbonate or sodium bicarbonate), or lower tertiary alkylamines, aralkylamines, aromatic amines or cycloalkylamines, (such as triethylamine, dimethylbenzylamine, pyridine, 1,5-diazabicyclo-[4.3.0]-non-5-ene (DBN) and 1,8-diazabicyclo-[5.4.0]-undec-7-ene (DBU)). However, it is also possible to employ an appropriate excess of azine of the formula (II).

In carrying out the elimination of hydrogen halide, the reaction temperatures can be varied in the same manner as has been described for the first stage of the process according to the invention.

In carrying out the process according to the invention, the starting materials of the formulae (II) and (III) are preferably employed in equimolar quantities. The isolation of the end products is effected according to customary methods.

The active compounds according to the invention influence plant growth and can therefore be used as defoliants, desiccants, agents for destroying broadleaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to a very good general herbicidal action, the active compounds according to the invention exhibit a good toleration to useful plants. Thus, it is possible to selectively combat important graminaceous weeds in important crops of useful plants, such as cotton, corn, soy beans and beet.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy-beans or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance, the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the forms prepared therefrom by further dilution, such as ready-to-use solutions, suspensions, emulsions, powders, pastes and granules. They are used in the customary manner, for example by watering, spraying, atomizing, scattering or dusting.

When the active compounds according to the invention are used as herbicides, the active compounds can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5 kg/ha, when the active compounds according to the invention are employed as herbicides; and between 0.01 and 50 kg of active compounds per ha, preferably between 0.05 and 10 kg/ha, when they are employed as plant growth regulators.

When the compounds according to the invention are employed as plant growth regulators, the rule is that they are applied within a preferred period of time, the exact definition of which depends on the climatic and vegetative circumstances.

The present invention also provides herbicidal or plant growth regulant composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods or providing a harvested crop may be improved by the present invention.

When used in appropriate quantities, the compounds according to the invention also exhibit fungicidal action, in particular against Oomycetes or against cereal diseases. In this context, they disclose not only a protective action, but in some cases also systemic action. Thus, it is possible to protect plants against attack by fungi if the active compounds are fed, via the soil and the root or via the seed, to the parts of the plant which are above the soil.

PREPARATION OF STARTING MATERIALS OF THE FORMULA (II)

EXAMPLE 1

(a)

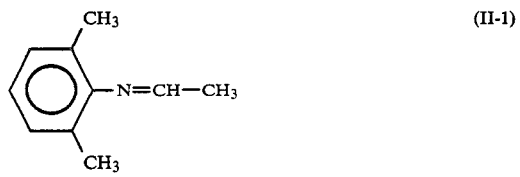

(II-1)

180 g (3 mols) of sodium sulphate and 3 ml of dimethylbenzylamine were added to 121 g (1 mol) of 2,6-dimethylaniline in 200 ml of methylene chloride. 88 g (2 mols) of acetaldehyde were added to the mixture at 0° C. The mixture was stirred at 0° C. for 4 hours and was filtered, and the filtrate was concentrated in vacuo at a maximum bath temperature of 20° C. 140 g (95.2% of theory) of N-ethylidene-2,6-dimethylaniline were obtained as a reddish oil.

(b)

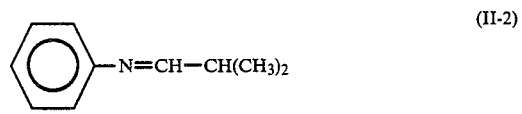

(II-2)

144 g (2 mols) of isobutyraldehyde were added dropwise to a solution of 92 g (1 mol) of aniline, 250 ml of methylene chloride, 2 ml of dimethylbenzylamine and 150 g of anhydrous magnesium sulphate at 0° C. in the course of 1 hour, whilst stirring. The mixture was further stirred at from 0° to 10° C. for 5 hours and was filtered, and the residue was rinsed with 200 ml of methylene chloride. The combined organic phases were freed from solvent, in vacuo, at from 30° to 40° C. 155 g of crude N-isobutylideneaniline were obtained and were directly further reacted.

(c)

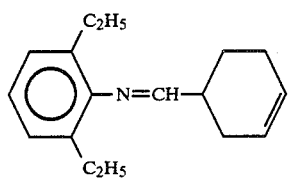
(II-3)

447 g (3 mols) of 2,6-diethylaniline and 327 g (3 mols) of cyclohex-3-ene-1-carboxaldehyde in 1,000 ml of toluene were heated under reflux for 9 hours in a water separator until water was no longer separated off. The reaction mixture was thereafter concentrated in vacuo by distilling off the solvent, and the residue was distilled in vacuo. 615 1 g (85% of theory) of N-(cyclohex-3-ethyl-methylidene)-2,6-diethylaniline of boiling point 110° to 112° C./0.1 mbar were obtained.

(d)

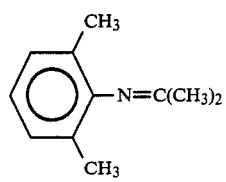
(II-4)

0.1 g of p-toluenesulphonic acid were added to a mixture of 121 g of dimethylaniline and 156 g (1.5 mol) of 2,2-dimethoxypropane and the mixture was heated under reflux for 30 minutes. The methanol formed was then distilled off. To complete the reaction, a further 52 g (0.5 mol) of 2,2-dimethoxypropane and 0.05 g of p-toluenesulphonic acid were added and the reaction mixture was distilled until the boiling point of the 2,2-dimethoxypropane (82° C.) was reached. The residual solution was concentrated in vacuo. 157 g (97% of theory) of N-isopropylidene-2,6-dimethylaniline were obtained in the form of a colourless oil.

(e)

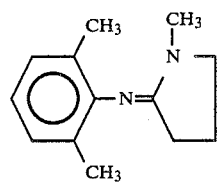
(II-5)

76.7 g (0.5 mol) of phorphorus oxychloride were added dropwise to a solution of 99.15 g (1 mol) of N-methylpyrrolidone in 375 ml of toluene at 20° to 25° C. The mixture was further stirred for 2 hours and a solution of 60.6 g (0.5 mol) of 2,6-dimethylaniline in 125 ml of toluene was then added dropwise at 20° to 30° C. The reaction mixture was then heated to 70° C. for 4 hours. After the mixture had cooled, the toluene phase was separated off, the remaining oily residue was taken up in water, and the solution was brought to pH 13 with aqueous sodium hydroxide solution and extracted several times with chloroform. The combined extracts were dried over sodium sulphate and concentrated. The resulting residue was distilled in vacuo.

98.7 g (40% of theory) of N-(N'-methyl-2-pyrrolidenyl)-2,6-dimethylaniline of boiling point 87° to 89° C./0.3 mbar were obtained.

The starting materials of the formula (II), listed in Table 1 below were obtained in an analogous manner:

TABLE 1

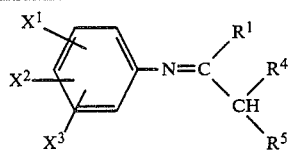
(II)

| Starting Material No. | $X^1$ | $X^2$ | $X^3$ | $R^1$ | $R^4$ | $R^5$ | Physical constants |
|---|---|---|---|---|---|---|---|
| (II-6) | 2-$C_2H_5$ | 6-$CH_3$ | H | H | H | H | Oil |
| (II-7) | 2-$C_2H_5$ | 6-$C_2H_5$ | H | H | H | H | Oil |
| (II-8) | 2-$C_2H_5$ | 6-$CH_3$ | H | $CH_3$ | H | H | Oil |
| (II-9) | 2-$CH_3$ | 6-$CH_3$ | H | H | $CH_3$ | $CH_3$ | B.p.: 108–110° C./20 mbar |
| (II-10) | 2-$CH_3$ | 6-$C_2H_5$ | H | H | $CH_3$ | $CH_3$ | B.p.: 112–115° C./20 mbar |
| (II-11) | 2-$C_2H_5$ | 6-$C_2H_5$ | H | H | $CH_3$ | $CH_3$ | B.p.: 123–125° C./20 mbar |
| (II-12) | 2-$CH_3$ | 6-$CH_3$ | H | H | =CH—$CH_3$ | | B.p.: 66° C./0.4 mbar |
| (II-13) | 2-$CH_3$ | 6-$CH_3$ | H | $CH_3$ | =C($CH_3$)$_2$ | | B.p.: 71–81° C./0.3 mbar |
| (II-14) | 2-$C_2H_5$ | 6-$C_2H_5$ | H | H | =CH—$CH_3$ | | B.p.: 125–128° C./7 mbar |
| (II-15) | 2-$CH_3$ | 6-$CH_3$ | H | H |  | | B.p.: 86° C./0.2 mbar |
| (II-16) | 2-$C_2H_5$ | 6-$C_2H_5$ | H | H |  | | B.p.: 110–112° C./0.15 mbar |

TABLE 1-continued (II) [structure: X¹, X², X³ substituted phenyl-N=C(R¹)-CH(R⁴)(R⁵)]

| Starting Material No. | X¹ | X² | X³ | R¹ | R⁴ | R⁵ | Physical constants |
|---|---|---|---|---|---|---|---|
| (II-17) | 2-CH₃ | 6-C₂H₅ | H | H | \multicolumn{2}{c}{cyclohexenyl} | B.p.: 107–110° C./0.5 mbar |
| (II-18) | 2-CH₃ | 6-CH₃ | H | H | \multicolumn{2}{c}{dihydropyranyl} | B.p.: 111° C./0.3 mbar |
| (II-19) | 2-CH₃ | 6-CH₃ | H | \multicolumn{2}{c}{=cyclopentylidene} | H | B.p.: 133–140° C./20 mbar |
| (II-20) | 2-CH₃ | 6-C₂H₅ | H | \multicolumn{2}{c}{=cyclopentylidene} | H | B.p.: 125–135° C./20 mbar |
| (II-21) | 2-CH₃ | 6-CH₃ | H | \multicolumn{2}{c}{=cyclohexylidene} | H | B.p.: 150–152° C./11 mbar |
| (II-22) | 2-CH₃ | 6-CH₃ | H | \multicolumn{2}{c}{=N-methylpiperidinylidene} | H | B.p.: 95° C./0.3 mbar |
| (II-23) | 2-CH₃ | 6-CH₃ | H | H | H | —CO—CH₃ | B.p.: 94° C./0.15 mbar |
| (II-24) | 2-CH₃ | 6-CH₃ | H | CH₃ | OCH₃ | OCH₃ | B.p.: 93° C./0.6 mbar |
| (II-25) | 2-CH₃ | 6-CH₃ | H | CH₃ | H | OCH₃ | B.p.: 70° C./0.2 mbar |
| (II-26) | 2-Cl | 6-CH₃ | H | \multicolumn{2}{c}{=cyclopentylidene} | H | B.p.: 142° C./16 mbar |
| (II-27) | 2-CH₃ | 6-CH₃ | H | H | H | —COOC₂H₅ | B.p.: 90–92° C./20 mbar |
| (II-28) | 2-CH₃ | 6-Cl | H | CH₃ | \multicolumn{2}{c}{=C(CH₃)₂} | B.p.: 80° C./0.1 mbar |
| (II-29) | 2-CH₃ | 6-CH₃ | H | \multicolumn{2}{c}{=pyrrolidinylidene(N)} | H | Oil |
| (II-30) | 2-CH₃ | 6-CH₃ | H | H | \multicolumn{2}{c}{=CH—C₆H₅} | M.p.: 69° C. |
| II-31 | 2-CH₃ | 6-CH₃ | H | H | H | C₂H₅ | B.p. 65° C./0.2 mbar |
| II-32 | 2-CH₃ | 6-CH₃ | H | H | \multicolumn{2}{c}{=CH—CH=CH—CH₃} | B.p. 85° C./0.4 mbar |
| II-33 | 2-CH₃ | 6-CH₃ | H | CH₃ | CH₃ | CH₃ | B.p. 64° C./0.2 mbar |
| II-34 | 2-CH₃ | 6-CH₃ | H | \multicolumn{2}{c}{=cyclopentylidene} | —COCH₃ | M.p. 55° C. |

TABLE 1-continued

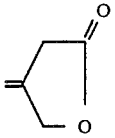

| Starting Material No. | X¹ | X² | X³ | R¹ | R⁴ | R⁵ | Physical constants |
|---|---|---|---|---|---|---|---|
| II-35 | 2-CH$_3$ | 6-CH$_3$ | H | | 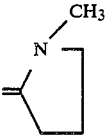 | H | M.p. 199° C. |
| II-36 | 2-CH$_3$ | 4-CH$_3$ | 6-CH$_3$ | CH$_3$ | H | H | Oil |
| II-37 | 3-Cl | 5-Cl | H | | 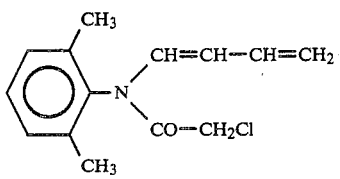 | H | Oil |
| II-38 | 2-CH$_3$ | 6-CH$_3$ | H | —C(CH$_3$)$_3$ | H | H | B.p. 58° C./0.1 mbar |

PREPARATION OF END PRODUCTS OF THE FORMULA (I)

EXAMPLE 2

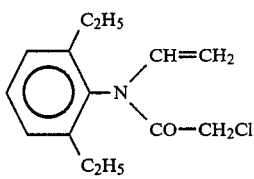 (1)

175 g (1 mol) of N-ethylidene-2,6-diethylaniline were added dropwise to a solution of 113 g (1 mol) of chloroacetyl chloride in 150 ml of toluene at −10° to 0° C. The mixture was further stirred at 0° C. for 3 hours and a solution of 101 g of triethylamine in 500 ml of toluene was then added dropwise, the temperature being kept at from −10° to 0° C. by cooling. The mixture was further stirred at room temperature for 2 hours, the precipitated triethylamine hydrochloride was filtered off under suction and rinsed with 100 ml of toluene, and the organic phase was concentrated in vacuo. The resulting oily residue was purified further by distillation or fractional crystallization from petroleum ether.

190 g (76% of theory) of N-vinyl-N-(2,6-diethylphenyl)-chloroacetamide were obtained as a pale yellow oil, of boiling point 97°–100° C./0.1 mbar, which slowly crystallized through (melting point 45° to 47° C.).

EXAMPLE 3

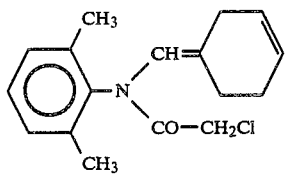 (2)

17.3 g (0.1 mol) of N-but-2-enylidene-2,6-dimethylaniline were added dropwise to a solution of 11.3 g (0.1 mol) of chloroacetyl chloride in 10 ml of toluene at 20° C. The mixture was further stirred at 20° C. for 1 hour and 10.1 g (0.1 mol) of triethylamine were then added dropwise. The mixture was further stirred at 20° C. for 1 hour and the precipitate which separated off was filtered off under suction. The filtrate was washed with dilute aqueous bicarbonate solution and then with water, and was subsequently concentrated in vacuo. The residue was recrystallized from hexane. 12.4 g (49.7% of theory) of N-(1,3-butadienyl)-N-(2,6-dimethylphenyl)chloroacetamide were obtained in the form of colorless crystals of melting point 88° C.

EXAMPLE 4

(3)

42.6 g (0.2 mol) of N-(3-cyclohexenyl-methylidene)-2,6-dimethylaniline were added dropwise to a solution of 22.6 g (0.2 mol) of chloroacetyl chloride in 50 ml of toluene at 20° C., while stirring. The mixture was further stirred for 15 hours and 20.2 g (0.2 mol) of triethylamine were then added dropwise at 20° C. The mixture was further stirred at 20° C. for 15 hours; the precipitate was then filtered off. The organic phase was first washed with dilute aqueous bicarbonate solution and then with water, and was finally concentrated in vacuo. The residue was extracted several times with petroleum ether. The combined extracts were concentrated in vacuo.

30.3 g (52.3% of theory) of N-(3-cyclohexenylidenemethyl)-N-(2,6-dimethylphenyl)-chloroacetamide were obtained in the form of a slightly yellow oil.

EXAMPLE 5

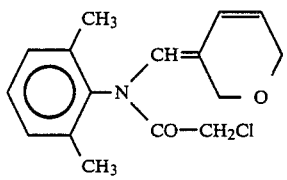
(4)

43 g (0.2 mol) of N-(2,3-dihydro-α-pyran-5-yl-methylidene)-2,6-dimethylaniline were added dropwise to a solution of 22.4 g (0.2 mol) of chloroacetyl chloride in 30 ml of toluene at 20° C., while stirring. The mixture was further stirred at 20° C. for 2 hours and 20.2 g (0.1 mol) of triethylamine were then added dropwise at 20° C. After the mixture had been further stirred for 1 hour at 20° C., it was filtered off under suction from the precipitated triethylamine hydrochloride, and the filtrate was first washed with dilute aqueous bicarbonate solution and then with water, and was finally concentrated in vacuo. The residue was recrystallized from petroleum ether.

38.2 g (65.4% of theory) of N-(2,3-dihydro-α-pyran-5-ylidenemethyl)-N-(2,6-dimethylphenyl)-chloroacetamide were obtained in the form of colorless crystals of melting point 80° C.

EXAMPLE 6

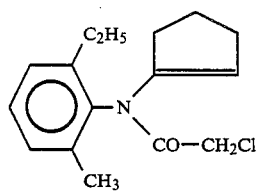
(5)

20.1 g (0.1 mol) of N-(cyclopentylidene)-2-ethyl-6-methyl-aniline were added dropwise to a solution of 11.3 g (0.1 mol) of chloroacetyl chloride in 10 ml of toluene at 20° C., while stirring. The mixture was further stirred at 20° C. for 2 hours and 15.2 g (0.1 mol) of diaza-bicyclo-undecane were then added dropwise. The reaction mixture was then further stirred at 20° C. for 1 hour and was poured into 200 ml of dilute aqueous bicarbonate solution. The organic phase was separated off, washed several times with water and then concentrated in vacuo. The product was then subjected to incipient distillation in a high vacuum in order to remove a residue of aniline.

15.7 g (56.7% of theory) of N-(cyclopent-1-enyl)-N-(2-ethyl-6-methyl-phenyl)-chloroacetamide were obtained in the form of a yellow oil.

EXAMPLE 7

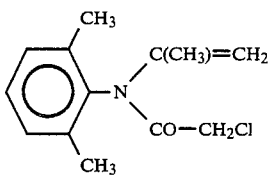
(6)

322.5 g (2 mols) of N-isopropylidene-2,6-dimethylaniline were added dropwise to a solution of 113 g (1 mol) of chloroacetyl chloride in 100 ml of toluene, the temperature being kept at 0° C. The mixture was then further stirred for another 3 hours at room temperature. The mixture was filtered off from the precipitate which separated out (N-isopropylidene-2,6-diethylamine hydrochloride), and the filtrate was first washed several times with aqueous bicarbonate solution and then with water. The organic phase was dried over sodium sulphate and concentrated in vacuo. The residue was fractionally distilled in vacuo.

180.6 g (76% of theory) of N-(1-methylvinyl)-N-(2,6-dimethylphenyl)-chloroacetamide were obtained as a oil of boiling point 98° to 106° C./0.15 mbar.

EXAMPLE 8

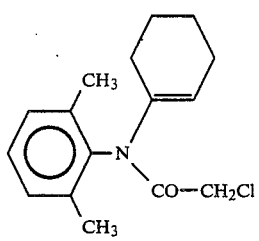
(7)

209 g (1 mol) of N-cyclohexylidene-2,6-dimethylaniline were added dropwise to a solution of 113 g (1 mol) of chloroacetyl chloride in 200 ml of toluene at from 0° C. to 10° C., while stirring. The mixture was further stirred at room temperature for 3 hours and was then heated under reflux until hydrogen chloride was no longer evolved. The solution was thereafter concentrated in vacuo. 21.9 g of a solid residue were obtained and fractionally recrystallized from ligroin.

18 g (65% of theory) of N-(cyclohex-1-enyl)-N-(2,6-dimethylphenyl)-chloroacetamide were obtained in the form of yellow-colored crystals of melting point 78° C.

The compounds of the formula (I), listed in Table 2 below, were obtained in an analogous manner;

TABLE 2

$$\begin{array}{c} X^1 \\ X^2 \\ X^3 \end{array} \diagdown \text{N} \diagup \begin{array}{c} R^1 \\ C=C \\ CO-CH_2Cl \end{array} \diagup \begin{array}{c} R^2 \\ R^3 \end{array} \quad (I)$$

| Compound No. | $X^1$ | $X^2$ | $X^3$ | $-CR^1=CR^2R^3$ | Physical constants |
|---|---|---|---|---|---|
| 8 | 2-$CH_3$ | 6-$CH_3$ | H | $-CH=CH_2$ | M.p.: 85° C. |
| 9 | 2-$C_2H_5$ | 6-$CH_3$ | H | $-CH=CH_2$ | B.p.: 90° C. |
| 10 | 2-$C_2H_5$ | 6-$CH_3$ | H | $-C(CH_3)=CH_2$ | B.p.: 93–97° C./0.1 mbar |
| 11 | 2-$CH_3$ | 6-$CH_3$ | H | $-C(CH_3)=CH-\underset{\underset{CH_2}{\parallel}}{C}-CH_3$ | Oil |
| 12 | 2-$CH_3$ | 6-$CH_3$ | H | (4-methyl-tetrahydropyridinylidene) | M.p.: 92° C. |
| 13 | 2-$CH_3$ | 6-$CH_3$ | H | (cyclohexenylidene) | Oil |
| 14 | 2-$CH_3$ | 6-$CH_3$ | H | $-CH=CH-CO-CH_3$ | M.p.: 147° C. |
| 15 | 2-Cl | 6-$CH_3$ | H | (cyclohexenylidene) | Oil |
| 16 | H | H | H | $-CH=C\diagup\!\!\!\!{}^{CH_3}_{CH_3}$ | M.p.: 85° C. |
| 17 | 2-$CH_3$ | 6-$CH_3$ | H | $-\underset{\underset{CH_3}{\mid}}{C}=CH-OCH_3$ | M.p.: 110° C. |
| 18 | 2-$CH_3$ | 6-Cl | H | $-\underset{\underset{CH_3}{\mid}}{C}=CH-\underset{\underset{CH_3}{\mid}}{C}=CH_2$ | Oil |
| 19 | 2-$CH_3$ | 6-$CH_3$ | H | $-CH=CH-C_2H_5$ | M.p.: 57° C. |
| 20 | 2-$CH_3$ | 6-$CH_3$ | H | $-CH=C(CH_3)_2$ | Oil |
| 21 | 2-$CH_3$ | 6-$CH_3$ | H | $-C(C_3H_7-i)=CH_2$ | Oil |
| 22 | 2-$CH_3$ | 6-$CH_3$ | H | $-C(C_4H_9-t)=CH_2$ | Oil |
| 23 | 2-$CH_3$ | 6-$CH_3$ | H | (butenolide =O, O) | M.p.: 176° C. |

The herbicidal and plant growth regulant activity of the compounds of this invention is illustrated by the following biotest-examples.

In these examples, the compounds according to the present invention are each identified by the number (given in brackets) from the corresponding preparative example and Table 2 hereinabove.

The known comparison compound is identified as follows:

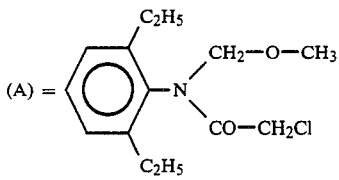

2,6-Diethyl-N-methoxymethyl-chloroacetanilide (disclosed in U.S. Pat. No. 3,442,945).

EXAMPLE 9

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0%=no action (like untreated control)
100%=total destruction

In this test, the active compounds (1), (6), (8), (9) and (10) according to the invention showed better selective activity than the compound (A) known from the state of the art.

EXAMPLE 10

Inhibition of growth of grass (*Festuca pratensis*)

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Grass (*Festuca pratensis*) was grown in a greenhouse up to a height in growth of 5 cm. In this stage, the plants were sprayed with the preparations of active compound until dripping wet. After 3 weeks, the additional growth was measured and the inhibition of growth in percent of the additional growth of the control plants was calculated. 100% inhibition of growth meant that growth had stopped and 0% denoted a growth corresponding to that of the control plants.

In this test, the active compound (8) according to the invention showed a very powerful inhibition of growth.

It will be appreciated that the instant specification and examples are set forth by way of illustration and not limitation, and that various modifications and changes may be made without departing from the spirit and scope of the present invention.

We claim:

1. An N-(alkenyl)-chloroacetanilide of the formula

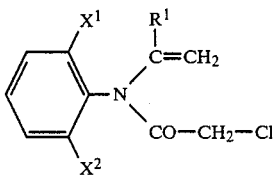

in which
$X^1$ and $X^2$ each individually is methyl or ethyl, and
$R^1$ is hydrogen or methyl.

2. A compound according to claim 1, wherein such compound is N-vinyl-N-(2,6-diethylphenyl)-chloroacetamide of the formula

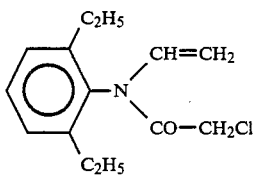

3. A compound according to claim 1, wherein such compound is N-(1-methylvinyl)-N-(2,6-dimethylphenyl)-chloroacetamide of the formula

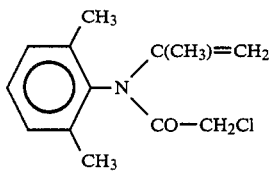

4. A compound according to claim 1, wherein such compound is N-vinyl-N-(2,6-dimethylphenyl)-chloroacetamide of the formula

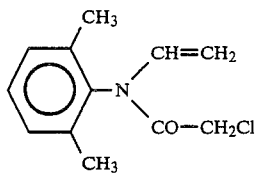

5. A compound according to claim 1, wherein such compound is N-vinyl-N-(2-methyl-6-ethylphenyl)-chloroacetamide of the formula

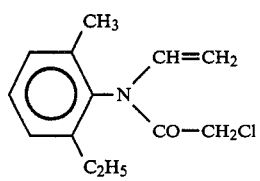

6. A compound according to claim 1, wherein such compound is N-(1-methylvinyl)-N-(2-methyl-6-ethylphenyl)-chloroacetamide of the formula

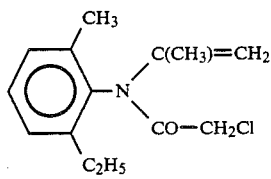

7. A plant-growth regulating composition comprising as active ingredient a plant-growth regulating effective amount of a compound according to claim 1 in admixture with a diluent.

8. A herbicidal composition comprising as active ingredient a herbicidally effective amount of a compound according to claim 1 in admixture with a diluent.

9. A method of combating weeds comprising applying to the weeds, or to a habitat thereof, herbicidally effective amount of a compound according to claim 1.

10. A method of regulating the growth of plants, comprising applying to the plants, or to a habitat thereof, a plant growth-regulating effective amount of a compound according to claim 1.

11. The method according to claim 9, wherein such compound is
N-vinyl-N-(2,6-diethylphenyl-chloroacetamide,
N-(1-methylvinyl)-N-(2,6-dimethylphenyl)-chloroacetamide,
N-vinyl-N-(2,6-dimethylphenyl)-chloroacetamide,
N-vinyl-N-(2-methyl-6-ethylphenyl)-chloroacetamide, or
N-(1-methylvinyl)-N-(2-methyl-6-ethylphenyl)-chloroacetamide.

12. The method according to claim 10, wherein such compound is
N-vinyl-N-(2,6-diethylphenyl-chloroacetamide,
N-(1-methylvinyl)-N-(2,6-dimethylphenyl)-chloroacetamide,
N-vinyl-N-(2,6-dimethylphenyl)-chloroacetamide,
N-vinyl-N-(2-methyl-6-ethylphenyl)-chloroacetamide, or
N-(1-methylvinyl)-N-(2-methyl-6-ethylphenyl)-chloroacetamide.

* * * * *